United States Patent
Valaie (10) Patent No.: US 9,398,946 B2
(45) Date of Patent: Jul. 26, 2016

(54) EXPANDABLE DEVICE FOR TREATMENT OF A STRICTURE IN A BODY VESSEL

(71) Applicant: Cook Medical Technologies LLC, Bloomington, IN (US)

(72) Inventor: Arman H. Valaie, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/825,683

(22) Filed: Aug. 13, 2015

(65) Prior Publication Data

US 2015/0342634 A1    Dec. 3, 2015

Related U.S. Application Data (62) Division of application No. 11/855,611, filed on Sep. 14, 2007, now Pat. No. 9,138,307.

(51) Int. Cl.
*A61M 29/00* (2006.01)
*A61F 2/01* (2006.01)
(Continued)

(52) U.S. Cl.
CPC ............. *A61F 2/013* (2013.01); *A61B 17/3207* (2013.01); *A61B 17/320725* (2013.01);
(Continued)

(58) Field of Classification Search
CPC ........... A61B 17/320725; A61B 2017/320775; A61B 17/3207; A61B 2017/00867; A61B 2017/320716; A61B 2017/00871; A61F 2/01; A61F 2/013; A61F 2002/018; A61F 2210/0014; A61F 2230/0091
USPC ............. 623/1.22, 1.11, 23.72; 606/159, 200; 604/104–107
See application file for complete search history.

(56) References Cited

U.S. PATENT DOCUMENTS

| | | |
|---|---|---|
| 3,108,593 A | 10/1963 | Glassman |
| 3,334,629 A | 8/1967 | Cohn |

(Continued)

FOREIGN PATENT DOCUMENTS

| | | |
|---|---|---|
| DE | 3429850 A1 | 2/1986 |
| EP | 1127556 A2 | 8/2001 |

(Continued)

OTHER PUBLICATIONS

Rubicon Embolic Filter, the Next Generation of EM, Rubicon Medical, www.rubiconmed.com.
(Continued)

*Primary Examiner* — Tuan V Nguyen
*Assistant Examiner* — Kevin Everage
(74) *Attorney, Agent, or Firm* — Brinks Gilson & Lione (57) ABSTRACT

An expandable and retrievable device for treatment of a stenotic lesion in a body vessel is disclosed. The device comprises a tubular portion including a proximal end and a distal end extending from the proximal end. The tubular portion has a lumen formed therethrough between the proximal and distal ends. The device further comprises an expandable member formed helically about the tubular portion. The expandable member is configured to helically close, defining a collapsed state for delivery of the device. The expandable member is configured to helically open, defining an expanded state for treatment of the stenotic lesion in the body vessel. The expandable member has at least one filter portion that helically extends from the tubular portion at a predetermined angle. This defines a proximally faced opening when the expandable member is in the expanded state.

6 Claims, 3 Drawing Sheets

(51) Int. Cl.
  *A61B 17/3207*  (2006.01)
  *A61B 17/00*  (2006.01)
  *A61M 25/00*  (2006.01)
  *A61M 25/06*  (2006.01)

(52) U.S. Cl.
  CPC .......... *A61B2017/00867* (2013.01); *A61B 2017/00871* (2013.01); *A61B 2017/320716* (2013.01); *A61F 2002/018* (2013.01); *A61F 2210/0014* (2013.01); *A61F 2230/0006* (2013.01); *A61F 2230/0067* (2013.01); *A61F 2230/0091* (2013.01); *A61M 25/00* (2013.01); *A61M 2025/0681* (2013.01)

(56) References Cited

U.S. PATENT DOCUMENTS

| | | |
|---|---|---|
| 3,472,230 A | 10/1969 | Fogarty |
| 3,547,103 A | 12/1970 | Cook |
| 3,635,223 A | 1/1972 | Klieman |
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,456,000 A | 6/1984 | Schjeldahl et al. |
| 4,494,531 A | 1/1985 | Gianturco |
| 4,548,206 A | 10/1985 | Osborne |
| 4,561,439 A | 12/1985 | Bishop et al. |
| 4,562,039 A | 12/1985 | Koehler |
| 4,604,094 A | 8/1986 | Shook |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,732,152 A | 3/1988 | Wallsten et al. |
| 4,817,600 A | 4/1989 | Herms et al. |
| 4,824,435 A | 4/1989 | Giesy et al. |
| 4,832,055 A | 5/1989 | Palestrant |
| 4,846,794 A | 7/1989 | Hertzer |
| 4,848,343 A | 7/1989 | Wallsten et al. |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 4,998,916 A | 3/1991 | Hammerslag et al. |
| 5,053,008 A | 10/1991 | Bajaj |
| 5,059,205 A | 10/1991 | El-Nounou et al. |
| 5,069,226 A | 12/1991 | Yamauchi et al. |
| 5,078,726 A | 1/1992 | Kreamer |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,129,910 A | 7/1992 | Phan et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,163,927 A | 11/1992 | Woker et al. |
| 5,203,772 A | 4/1993 | Hammerslag et al. |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,397 A | 9/1994 | Palermo et al. |
| 5,350,398 A | 9/1994 | Pavcnik et al. |
| 5,364,345 A | 11/1994 | Lowery et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,451,233 A | 9/1995 | Yock |
| 5,458,573 A | 10/1995 | Summers |
| 5,522,881 A | 6/1996 | Lentz |
| 5,527,338 A | 6/1996 | Purdy |
| 5,531,788 A | 7/1996 | Dibie et al. |
| 5,549,551 A | 8/1996 | Peacock et al. |
| 5,549,626 A | 8/1996 | Miller et al. |
| 5,556,414 A | 9/1996 | Turi |
| 5,562,698 A | 10/1996 | Parker |
| 5,571,135 A | 11/1996 | Fraser et al. |
| 5,591,195 A | 1/1997 | Taheri et al. |
| 5,601,595 A | 2/1997 | Smith |
| 5,624,461 A | 4/1997 | Mariant |
| 5,626,605 A | 5/1997 | Irie et al. |
| 5,630,797 A | 5/1997 | Diedrich et al. |
| 5,634,942 A | 6/1997 | Chevillon et al. |
| 5,649,953 A | 7/1997 | Lefebvre |
| 5,662,703 A | 9/1997 | Yurek et al. |
| 5,669,933 A | 9/1997 | Simon et al. |
| 5,681,347 A | 10/1997 | Cathcart et al. |
| 5,690,642 A | 11/1997 | Osborne et al. |
| 5,690,667 A | 11/1997 | Gia |
| 5,693,067 A | 12/1997 | Purdy |
| 5,693,087 A | 12/1997 | Parodi |
| 5,695,518 A | 12/1997 | Laerum |
| 5,695,519 A | 12/1997 | Summers et al. |
| 5,700,253 A | 12/1997 | Parker |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,738,667 A | 4/1998 | Solar |
| 5,746,767 A | 5/1998 | Smith |
| 5,755,772 A | 5/1998 | Evans et al. |
| 5,755,790 A | 5/1998 | Chevillon et al. |
| 5,766,203 A | 6/1998 | Imran et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,027 A | 9/1998 | Hassett et al. |
| 5,814,064 A | 9/1998 | Daniel et al. |
| 5,820,592 A | 10/1998 | Hammerslag |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,882,329 A | 3/1999 | Patterson et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,702 A | 6/1999 | Romley et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |

(56) References Cited

U.S. PATENT DOCUMENTS

| | | |
|---|---|---|
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,984,965 A | 11/1999 | Knapp et al. |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscroft et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,813 A | 5/2000 | Vrba et al. |
| 6,059,814 A | 5/2000 | Ladd |
| 6,063,113 A | 5/2000 | Kavteladze et al. |
| 6,066,158 A | 5/2000 | Engelson et al. |
| 6,068,645 A | 5/2000 | Tu |
| 6,074,357 A | 6/2000 | Kaganov et al. |
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |
| 6,093,199 A | 7/2000 | Brown et al. |
| 6,096,053 A | 8/2000 | Bates |
| 6,096,070 A | 8/2000 | Ragheb et al. |
| 6,099,549 A | 8/2000 | Bosma et al. |
| 6,106,497 A | 8/2000 | Wang |
| 6,126,672 A | 10/2000 | Berryman et al. |
| 6,126,673 A | 10/2000 | Kim et al. |
| 6,129,739 A | 10/2000 | Khosravi |
| 6,136,016 A | 10/2000 | Barbut et al. |
| 6,146,396 A | 11/2000 | Konya et al. |
| 6,146,404 A | 11/2000 | Kim et al. |
| 6,152,931 A | 11/2000 | Nadal et al. |
| 6,152,946 A | 11/2000 | Broome et al. |
| 6,152,947 A | 11/2000 | Ambrisco et al. |
| 6,156,061 A | 12/2000 | Wallace et al. |
| 6,156,062 A | 12/2000 | McGuinness |
| 6,159,230 A | 12/2000 | Samuels |
| 6,165,179 A | 12/2000 | Cathcart et al. |
| 6,165,198 A | 12/2000 | McGurk et al. |
| 6,165,199 A | 12/2000 | Barbut |
| 6,165,200 A | 12/2000 | Tsugita et al. |
| 6,168,579 B1 | 1/2001 | Tsugita et al. |
| 6,168,603 B1 | 1/2001 | Leslie et al. |
| 6,168,610 B1 | 1/2001 | Marin et al. |
| 6,168,622 B1 | 1/2001 | Mazzocchi |
| 6,171,327 B1 | 1/2001 | Daniel et al. |
| 6,171,328 B1 | 1/2001 | Addis |
| 6,174,318 B1 | 1/2001 | Bates et al. |
| 6,179,851 B1 | 1/2001 | Barbut et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,193,739 B1 | 2/2001 | Chevillon et al. |
| 6,203,561 B1 | 3/2001 | Ramee et al. |
| 6,206,931 B1 | 3/2001 | Cook et al. |
| 6,214,025 B1 | 4/2001 | Thistle et al. |
| 6,214,026 B1 | 4/2001 | Lepak et al. |
| 6,221,091 B1 | 4/2001 | Khosravi |
| 6,224,620 B1 | 5/2001 | Maahs |
| 6,231,588 B1 | 5/2001 | Zadno-Azizi |
| 6,231,589 B1 | 5/2001 | Wessman et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,092 B1 | 6/2001 | Qin et al. |
| 6,251,122 B1 | 6/2001 | Tsukernik |
| 6,254,550 B1 | 7/2001 | McNamara et al. |
| 6,254,633 B1 | 7/2001 | Pinchuk et al. |
| 6,258,026 B1 | 7/2001 | Ravenscroft et al. |
| 6,258,115 B1 | 7/2001 | Dubrul |
| 6,258,120 B1 | 7/2001 | McKenzie et al. |
| 6,261,305 B1 | 7/2001 | Marotta et al. |
| 6,264,672 B1 | 7/2001 | Fisher |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,277,125 B1 | 8/2001 | Barry et al. |
| 6,277,126 B1 | 8/2001 | Barry et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,710 B1 | 9/2001 | Cryer et al. |
| 6,299,604 B1 | 10/2001 | Ragheb et al. |
| 6,306,163 B1 | 10/2001 | Fitz |
| 6,309,399 B1 | 10/2001 | Barbut et al. |
| 6,312,444 B1 | 11/2001 | Barbut |
| 6,319,268 B1 | 11/2001 | Ambrisco et al. |
| 6,325,815 B1 | 12/2001 | Kusleika et al. |
| 6,325,816 B1 | 12/2001 | Fulton, III et al. |
| 6,328,755 B1 | 12/2001 | Marshall |
| 6,331,183 B1 | 12/2001 | Suon |
| 6,331,184 B1 | 12/2001 | Abrams |
| 6,334,864 B1 | 1/2002 | Amplatz et al. |
| 6,336,934 B1 | 1/2002 | Gilson et al. |
| 6,338,739 B1 | 1/2002 | Datta et al. |
| 6,340,364 B2 | 1/2002 | Kanesaka |
| 6,342,062 B1 | 1/2002 | Suon et al. |
| 6,342,063 B1 | 1/2002 | DeVries et al. |
| 6,344,048 B1 | 2/2002 | Chin et al. |
| 6,344,049 B1 | 2/2002 | Levinson et al. |
| 6,346,116 B1 | 2/2002 | Brooks et al. |
| 6,348,041 B1 | 2/2002 | Klint |
| 6,348,063 B1 | 2/2002 | Yassour et al. |
| 6,350,271 B1 | 2/2002 | Kurz et al. |
| 6,355,051 B1 | 3/2002 | Sisskind et al. |
| 6,358,228 B1 | 3/2002 | Tubman et al. |
| 6,361,545 B1 | 3/2002 | Macoviak et al. |
| 6,361,546 B1 | 3/2002 | Khosravi |
| 6,361,547 B1 | 3/2002 | Hieshima |
| 6,364,895 B1 | 4/2002 | Greenhalgh |
| 6,364,896 B1 | 4/2002 | Addis |
| 6,368,338 B1 | 4/2002 | Konya et al. |
| 6,371,961 B1 | 4/2002 | Osborne et al. |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,379,374 B1 | 4/2002 | Hieshima et al. |
| 6,380,457 B1 | 4/2002 | Yurek et al. |
| 6,383,146 B1 | 5/2002 | Klint |
| 6,383,171 B1 | 5/2002 | Gifford et al. |
| 6,383,174 B1 | 5/2002 | Eder |
| 6,383,193 B1 | 5/2002 | Cathcart et al. |

(56) References Cited

U.S. PATENT DOCUMENTS

| | | |
|---|---|---|
| 6,383,196 B1 | 5/2002 | Leslie et al. |
| 6,383,205 B1 | 5/2002 | Samson et al. |
| 6,383,206 B1 | 5/2002 | Gillick et al. |
| 6,391,044 B1 | 5/2002 | Yadav et al. |
| 6,391,045 B1 | 5/2002 | Kim et al. |
| 6,391,052 B2 | 5/2002 | Buirge et al. |
| 6,395,014 B1 | 5/2002 | Macoviak et al. |
| 6,402,771 B1 | 6/2002 | Palmer et al. |
| 6,402,772 B1 | 6/2002 | Amplatz et al. |
| 6,409,742 B1 | 6/2002 | Fulton, III et al. |
| 6,413,235 B1 | 7/2002 | Parodi |
| 6,416,530 B2 | 7/2002 | DeVries et al. |
| 6,419,686 B1 | 7/2002 | McLeod et al. |
| 6,423,052 B1 | 7/2002 | Escano |
| 6,423,086 B1 | 7/2002 | Barbut et al. |
| 6,425,909 B1 | 7/2002 | Dieck et al. |
| 6,428,557 B1 | 8/2002 | Hilaire |
| 6,428,558 B1 | 8/2002 | Jones et al. |
| 6,428,559 B1 | 8/2002 | Johnson |
| 6,432,122 B1 | 8/2002 | Gilson et al. |
| 6,436,112 B2 | 8/2002 | Wensel et al. |
| 6,436,120 B1 | 8/2002 | Meglin |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma et al. |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,454,775 B1 | 9/2002 | Demarais et al. |
| 6,458,139 B1 | 10/2002 | Palmer et al. |
| 6,458,145 B1 | 10/2002 | Ravenscroft et al. |
| 6,461,370 B1 | 10/2002 | Gray et al. |
| 6,468,290 B1 | 10/2002 | Weldon et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,500 B1 | 11/2002 | Kokish et al. |
| 6,485,501 B1 | 11/2002 | Green |
| 6,485,502 B2 | 11/2002 | Don Michael et al. |
| 6,491,712 B1 | 12/2002 | O'Connor |
| 6,494,895 B2 | 12/2002 | Addis |
| 6,497,709 B1 | 12/2002 | Heath |
| 6,499,487 B1 | 12/2002 | McKenzie et al. |
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,520,983 B1 | 2/2003 | Colgan et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |

(56) References Cited

U.S. PATENT DOCUMENTS

| | | |
|---|---|---|
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 | 2/2004 | Boyle et al. |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,855 B2 | 6/2004 | Yurek et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,855,154 B2 | 2/2005 | Abdel-Gawwad |
| 6,866,677 B2 | 3/2005 | Douk et al. |
| 6,866,680 B2 | 3/2005 | Yassour et al. |
| 6,872,211 B2 | 3/2005 | White et al. |
| 6,878,153 B2 | 4/2005 | Linder et al. |
| 6,896,691 B2 | 5/2005 | Boylan et al. |
| 6,929,709 B2 | 8/2005 | Smith |
| 6,932,831 B2 | 8/2005 | Forber |
| 6,936,059 B2 | 8/2005 | Belef |
| 6,939,361 B1 | 9/2005 | Kleshinski |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,469 B2 | 12/2005 | Broome et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | Van Der Burg et al. |
| 7,166,120 B2 | 1/2007 | Kusleika |
| 7,174,636 B2 | 2/2007 | Lowe |
| 7,189,249 B2 | 3/2007 | Hart et al. |
| 7,204,847 B1 | 4/2007 | Gambale |
| 7,220,271 B2 | 5/2007 | Clubb et al. |
| 7,255,687 B2 | 8/2007 | Huang et al. |
| 7,285,130 B2 | 10/2007 | Austin |
| 7,303,575 B2 | 12/2007 | Ogle |
| 7,306,619 B1 | 12/2007 | Palmer |
| 7,371,248 B2 | 5/2008 | Dapolito et al. |
| 7,393,358 B2 | 7/2008 | Malewicz |
| 7,601,162 B2 | 10/2009 | Hassler et al. |
| 7,604,649 B2 | 10/2009 | McGuckin et al. |
| 7,666,216 B2 | 2/2010 | Hogendijk et al. |
| 7,708,770 B2 | 5/2010 | Linder et al. |
| 7,731,722 B2 | 6/2010 | Lavelle et al. |
| 7,731,731 B2 | 6/2010 | Abela |
| 7,766,934 B2 | 8/2010 | Pal et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002383 A1 | 1/2002 | Sepetka et al. |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1 | 7/2002 | Becker et al. |
| 2002/0099435 A1 | 7/2002 | Stinson |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |

(56) References Cited

U.S. PATENT DOCUMENTS

| | | |
|---|---|---|
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1 | 11/2002 | Eum et al. |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004537 A1 | 1/2003 | Boyle et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucek |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Don Michael |
| 2003/0055452 A1 | 3/2003 | Joergensen et al. |
| 2003/0055480 A1 | 3/2003 | Fischell et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0065355 A1 | 4/2003 | Weber |
| 2003/0065356 A1 | 4/2003 | Tsugita et al. |
| 2003/0069596 A1 | 4/2003 | Eskuri |
| 2003/0073979 A1 | 4/2003 | Naimark et al. |
| 2003/0074019 A1 | 4/2003 | Gray et al. |
| 2003/0074054 A1 | 4/2003 | Duerig et al. |
| 2003/0078614 A1 | 4/2003 | Salahieh et al. |
| 2003/0083608 A1 | 5/2003 | Evans et al. |
| 2003/0083692 A1 | 5/2003 | Vrba et al. |
| 2003/0083693 A1 | 5/2003 | Daniel et al. |
| 2003/0088211 A1 | 5/2003 | Anderson et al. |
| 2003/0088266 A1 | 5/2003 | Bowlin |
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0109916 A1 | 6/2003 | Don Michael |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171800 A1 | 9/2003 | Bicek et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |

(56) References Cited

U.S. PATENT DOCUMENTS

| | | |
|---|---|---|
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212431 A1 | 11/2003 | Brady et al. |
| 2003/0212432 A1 | 11/2003 | Khairkhahan et al. |
| 2003/0212433 A1 | 11/2003 | Ambrisco et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225418 A1 | 12/2003 | Esksuri et al. |
| 2003/0225435 A1 | 12/2003 | Huter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006365 A1 | 1/2004 | Brady et al. |
| 2004/0006370 A1 | 1/2004 | Tsugita |
| 2004/0015152 A1 | 1/2004 | Day |
| 2004/0039412 A1 | 2/2004 | Isshiki et al. |
| 2004/0049226 A1 | 3/2004 | Keegan et al. |
| 2004/0054394 A1 | 3/2004 | Lee |
| 2004/0054395 A1 | 3/2004 | Lee et al. |
| 2004/0059372 A1 | 3/2004 | Tsugita |
| 2004/0064067 A1 | 4/2004 | Ward |
| 2004/0064179 A1 | 4/2004 | Linder et al. |
| 2004/0068271 A1 | 4/2004 | McAlister |
| 2004/0078044 A1 | 4/2004 | Kear |
| 2004/0082962 A1 | 4/2004 | Demarais et al. |
| 2004/0088038 A1 | 5/2004 | Dehnad et al. |
| 2004/0093009 A1 | 5/2004 | Denison et al. |
| 2004/0093012 A1 | 5/2004 | Cully et al. |
| 2004/0093016 A1 | 5/2004 | Root et al. |
| 2004/0093059 A1 | 5/2004 | Lee et al. |
| 2004/0098022 A1 | 5/2004 | Barone |
| 2004/0098026 A1 | 5/2004 | Joergensen et al. |
| 2004/0098033 A1 | 5/2004 | Leeflang et al. |
| 2004/0098112 A1 | 5/2004 | DiMatteo et al. |
| 2004/0102719 A1 | 5/2004 | Keith et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0138696 A1 | 7/2004 | Drasler et al. |
| 2004/0153118 A1 | 8/2004 | Clubb et al. |
| 2004/0158278 A1 | 8/2004 | Becker et al. |
| 2004/0162576 A1 | 8/2004 | Barbut et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0199201 A1 | 10/2004 | Kellett et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0021125 A1 | 1/2005 | Stack et al. |
| 2005/0027345 A1 | 2/2005 | Horan et al. |
| 2005/0038468 A1 | 2/2005 | Panetta et al. |
| 2005/0038503 A1 | 2/2005 | Greenhaigh |
| 2005/0043743 A1 | 2/2005 | Dennis |
| 2005/0043756 A1 | 2/2005 | Lavelle et al. |
| 2005/0043780 A1 | 2/2005 | Gifford et al. |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009798 A1 | 1/2006 | Callister et al. |
| 2006/0009799 A1 | 1/2006 | Kleshinski et al. |
| 2006/0020334 A1 | 1/2006 | Lashinski et al. |
| 2006/0025804 A1 | 2/2006 | Krolik et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0142845 A1 | 6/2006 | Molaei et al. |
| 2006/0161186 A1 | 7/2006 | Hassler et al. |
| 2006/0161241 A1 | 7/2006 | Barbut et al. |
| 2006/0184194 A1* | 8/2006 | Pal .................... A61F 2/013 606/200 |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287667 A1 | 12/2006 | Abela |
| 2006/0287668 A1 | 12/2006 | Fawzi et al. |
| 2007/0038241 A1 | 2/2007 | Pal |
| 2007/0066991 A1 | 3/2007 | Magnuson |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0149996 A1 | 6/2007 | Coughlin |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |
| WO | WO 2006/138391 A2 | 12/2006 |

OTHER PUBLICATIONS

Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.
Grummon, David S. et al., Appl. Phys. Lett., 82, 2727 (2003), pp. 2727.

* cited by examiner

EXPANDABLE DEVICE FOR TREATMENT OF A STRICTURE IN A BODY VESSEL

CROSS-REFERENCE TO RELATED APPLICATIONS

This application is a Divisional of U.S. patent application Ser. No. 11/855,611, filed Sep. 14, 2007, entitled "EXPANDABLE DEVICE FOR TREATMENT OF A STRICTURE IN A BODY VESSEL". The entire contents of which are incorporated herein by reference.

BACKGROUND OF THE INVENTION

The present invention relates to medical devices and particularly the present invention relates to an expandable device for treating a stricture in a body vessel.

Treatments for a stenotic lesion are continuously being improved. One example is the treatment for carotid artery stenosis. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery. Plaque forms when cholesterol, fat and other substances form in the inner lining of an artery. This formation process is called atherosclerosis.

Depending on the degree of stenosis and the patient's overall condition, carotid artery stenosis has been treated with surgery. The procedure (with its inherent risks) is called carotid endarterectomy, which removes the plaque from the arterial walls. Carotid endarterectomy has proven to benefit patients with arteries substantially narrowed, e.g., by about 70% or more. For people with less narrowed arteries, e.g., less than about 50%, an anti-clotting drug may be prescribed to reduce the risk of ischemic stroke. Examples of these drugs are anti-platelet agents and anticoagulants.

Carotid angioplasty is a more recently developed treatment for carotid artery stenosis. This treatment uses balloons and/or stents to open a narrowed artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon is then removed and exchanged via catheter for a stent delivery device. Once in position, a stent is deployed across the stenotic area. If needed, an additional balloon can be placed inside the deployed stent for post-dilation to make sure the struts of the stent are pressed firmly against the inner surface of the vessel wall.

Currently, devices such as stents used for treatment of a stenosis are typically permanent devices when deployed in a body vessel. In many situations, when a stenosis condition has passed, the deployed stent can not be removed from the patient. Thus, there is a need to provide a retrievable device, e.g., a stent, for treatment of a stenosis or stricture in a body vessel without compromising the cross-sectional profile of the device.

BRIEF SUMMARY OF THE INVENTION

The present invention generally provides an expandable and retrievable device for treatment of a stricture in a body vessel. The device has a reduced cross-sectional profile and is configured to conform to the tortuosity of blood vessels. This provides the ability for retrieval and an enhanced flexibility for access to more tortuous lumen areas with a body vessel.

In one embodiment, the present invention provides an expandable device for treatment of a stenotic lesion in a body vessel. The device comprises a tubular portion including a proximal end and a distal end extending from the proximal end. The tubular portion has a lumen formed therethrough between the proximal and distal ends. The device further comprises an expandable member formed helically about the tubular portion. The expandable member is configured to helically close, defining a collapsed state for delivery of the device. The expandable member is configured to helically open, defining an expanded state for treatment of the stenotic lesion in the body vessel. The expandable member has at least one filter portion that helically extends from the tubular portion at a predetermined angle. This defines a proximally faced opening when the expandable member is in the expanded state.

In another embodiment, the present invention provides an assembly for treatment of a stricture in a body vessel. The assembly comprises an inner catheter having a tubular body portion. The assembly further comprises an outer catheter having a distal end through which the inner catheter is disposed for deployment in the body vessel. The assembly further comprises the expandable device coaxially disposed within the inner catheter for treatment of the stricture in the body vessel.

In another example, the present invention provides a method for treating a stricture in a body vessel. The method comprises percutaneously introducing an inner catheter in the body vessel. The inner catheter has a tubular body portion. The method further comprises disposing the expandable device for treatment of the stricture in the body vessel. The device is in a collapsed state and is coaxially within the inner catheter. The method further comprises deploying the device in the expanded state at the stricture of the body vessel to treat the stricture.

Further objects, features, and advantages of the present invention will become apparent from consideration of the following description and the appended claims when taken in connection with the accompanying drawings.

BRIEF DESCRIPTION OF THE DRAWINGS

FIG. 3b is an exploded view of the assembly in FIG. 3a.

DETAILED DESCRIPTION OF THE INVENTION

The present invention generally provides an expandable device, e.g., a stent, having a reduced cross-sectional profile and configured to conform to tortuosity of blood vessels, allowing for the device to be more easily advanced through body vessels and providing an enhanced flexibility for access to more tortuous lumen areas within the body vessels. The device has a tubular portion and an expandable member formed helically about the tubular portion. The expandable member has at least one member portion, preferably a plurality of separate member portions, helically extending from the tubular portion at a predetermined angle. The separate member portions allow the tubular portion to maintain its flexibility as it is disposed through a tortuous body vessel. When helically closed, the device may be delivered through a body vessel. Upon deployment in a body vessel, the expandable member self-expands and helically opens.

Figure 1:
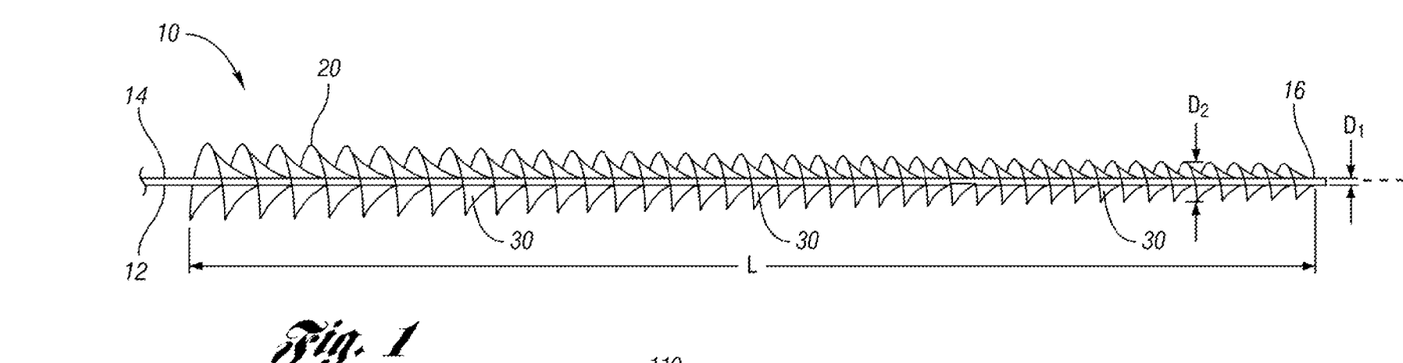
FIG. 1 is a side view of an expandable device for treating a stricture of a body vessel in accordance with one embodiment of the present invention.

FIG. 1 illustrates an expandable device 10 for treating a stricture in a body vessel in accordance with one embodiment of the present invention. As shown, the device 10 comprises a tubular portion 12 about which an expandable member 20 is formed. The expandable member 20 may be helically closed to define a collapsed state and helically opened to define an opened state.

As mentioned above, the device 10 comprises a tubular portion 12 having a first diameter $D_1$. As illustrated in FIG. 1, the tubular portion 12 includes a proximal portion 14 and a distal portion 16 extending from the proximal portion 14. The tubular portion 12 is preferably a tubular member for enhanced flexibility and to allow for a wire guide to be advanced therethrough.

This may be accomplished by any suitable means such as by machining the expandable member 20 helically around the tubular portion 12 disposed about a mandrel. However, any other way of forming the expandable member 20 helically about the tubular portion 12 may be used without falling beyond the scope or spirit of the present invention.

Figure 2:
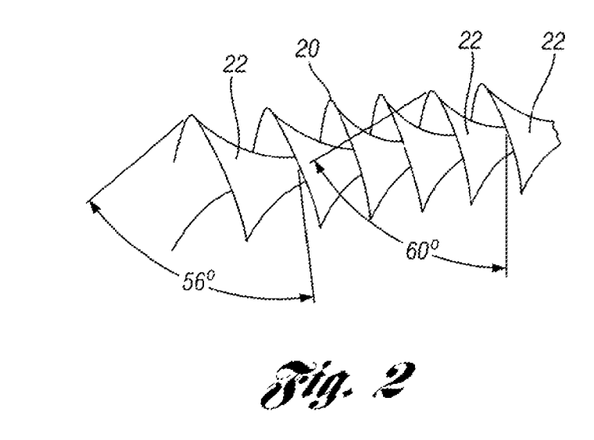
FIG. 2 is an enlarged view of the device of FIG. 1.

FIGS. 1 and 2 depict the device 10 further comprising an expandable member 20 formed helically about the tubular portion 12. In this embodiment, the expandable member 20 is configured to helically close, defining a collapsed state for delivery and retrieval of the device 10. Moreover, the expandable member 20 is configured to helically open to define an expanded state for treating a stricture in the body vessel. The expandable member 20 occupies a second diameter $D_2$ that varies based on the expanded and collapsed state thereof.

As shown in FIG. 2, the expandable member 20 comprises at least one member portion 30, preferably a plurality of member portions 30, each of which is integrally formed with another member portion 30. Each member portion 30 is helically formed and outwardly extends separately from the tubular portion 12 at a predetermined angle defining a proximally faced opening when the member is in an expanded state. In one embodiment, the predetermined angle is between about 40 and 70 degrees and preferably between about 55 and 65 degrees.

As shown, each of the plurality of member portions 30 is in coaxial alignment with each other about the tubular portion 12. Preferably, each member portion 30 is helically formed integrally with the tubular portion 12 and separately extends therefrom. This allows the tubular portion 12 to maintain its flexibility with the first diameter $D_1$ for advancement through tortuous areas within a body vessel.

FIGS. 1 and 2 illustrate that the expandable member 20 and the tubular portion 12 are formed along a longitudinal axis. The expandable member 20 may be helically closed in the collapsed state when the tubular portion 12 or the expandable member 20 is rotated about the longitudinal axis in a first direction. The expandable member 20 may be helically opened in the expanded state when the tubular portion 12 or the expandable member 20 is rotated about the longitudinal axis in a second direction.

As mentioned above, the device may be made of shape memory material, or may be configured to have shape memory defining the predetermined shape thereof in the deployed state. For example, the device may be comprised of any suitable material such as a pre-configured polymeric material, superelastic material, stainless steel wire, cobalt-chromium-nickel-molybdenum-iron alloy, or cobalt-chrome alloy. In one example, the device may be made of pre-configured polymeric material which takes on a predetermined shape, e.g. helical, when in the expanded state.

It is understood that the device may be formed of any other suitable material that may result in a self-opening or self-expanding device, such as shape memory materials or alloys. Shape memory alloys have the desirable property of becoming rigid, i.e., returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one example, the device is made from material including Nitinol with a transition temperature that is slightly below normal body temperature of humans, which is about 98.6° F. Thus, when the device 10 is deployed and exposed to normal body temperature, the alloy of the device will transform to austenite, that is, the remembered state, which for one embodiment of the present invention is the expanded state when deployed in the body vessel. To remove the device, the device is cooled to transform the material to martensite which is more ductile than austenite, making the device more malleable. As such, the device can be more easily collapsed and pulled into a lumen of a catheter for removal.

Figure 3A:
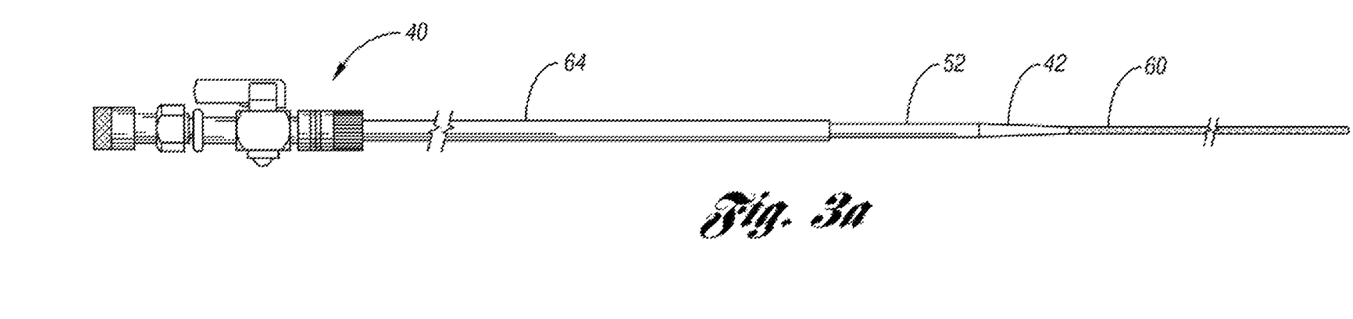
FIG. 3a is a side view of an assembly for treating a stricture in a body vessel in accordance with one embodiment of the present invention.
Figure 3B:
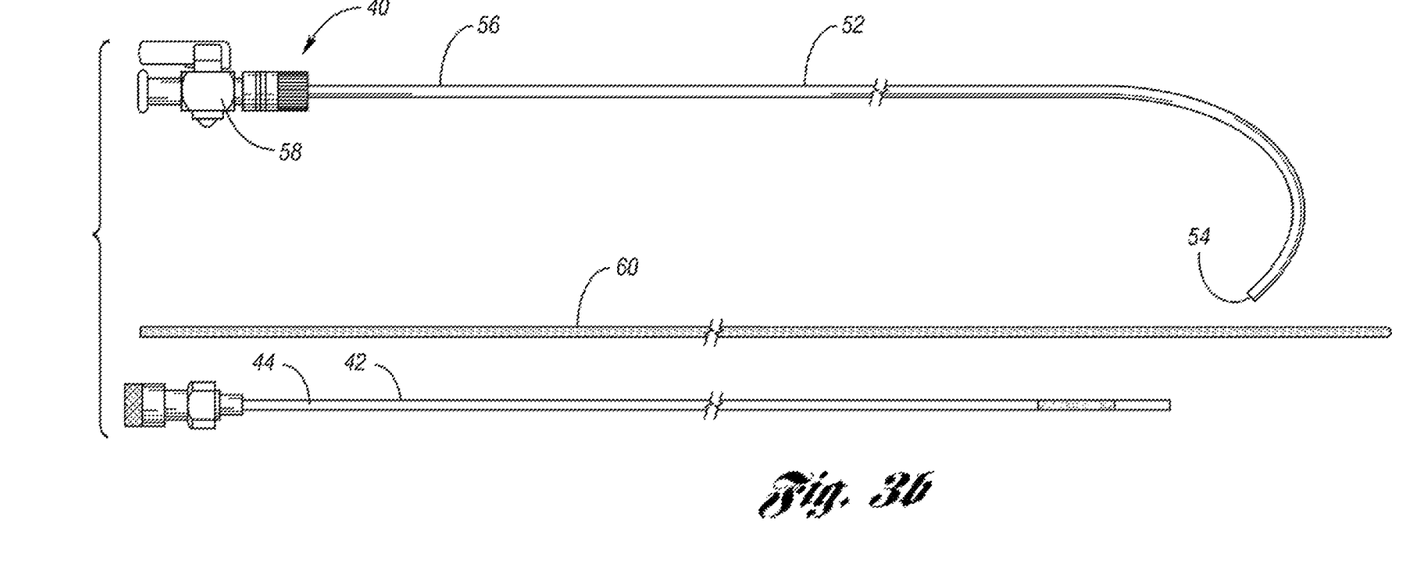

FIGS. 3a and 3b depict an assembly 40 for treatment of a stricture in a body vessel in accordance with another embodiment of the present invention. As shown, the assembly 40 comprises an inner catheter 42 having a tubular body 44. In this embodiment, the assembly 40 comprises the expandable device mentioned above. The tubular body 44 is preferably made of soft flexible material such as silicon or any other suitable material. In this embodiment, the catheter 42 includes an inner lumen. The inner lumen is formed therethrough for percutaneous guidance through the body vessel.

As shown, the assembly 40 further includes an outer catheter 52 having a distal end 54 through which the inner catheter 42 is disposed for deployment in the body vessel. The outer catheter 52 is preferably made of a soft, flexible material such as silicon or any other suitable material. Generally, the outer catheter 52 further has a proximal end 56 and a plastic adaptor or hub 58 to receive the expandable device and inner catheter 42 to be advanced therethrough. The size of the outer catheter 52 is based on the size of the body vessel in which it percutaneously inserts, and the size of the inner catheter 42.

As shown, the assembly 40 may also include a wire guide 60 configured to be percutaneously inserted within the vasculature to guide the outer catheter 52 to a location proximal to a stricture in a body vessel. The wire guide 60 provides the outer catheter 52 (and inner catheter 42) a path during insertion within the body vessel. The size of the wire guide 60 is based on the inside diameter of the outer catheter 52.

As shown, the expandable device is coaxially disposed through the inner lumen of the inner catheter 42 prior to treatment of the stricture in the body vessel. The expandable device is guided through the inner lumen preferably from the hub 58 and distally beyond the inner catheter 42, exiting from the distal end of the inner catheter 42 to a location within the vasculature upstream of the stricture to be stented.

In this embodiment, the apparatus further includes a polytetrafluoroethylene (PTFE) introducer sheath 64 for percutaneously introducing the wire guide 60 and the outer catheter 52 in a body vessel. Of course, any other suitable material may be used without falling beyond the scope or spirit of the present invention. The introducer sheath 64 may have any suitable size, e.g., between about three-french to eight-french. The introducer serves to allow the inner and inner catheters 42 to be percutaneously inserted to a desired location in the body vessel. The introducer sheath 64 receives the outer catheter 52 and provides stability to the inner catheter at a desired location of the body vessel. For example, the introducer sheath 64 is held stationary within a common visceral artery, and adds stability to the outer catheter 52, as the outer catheter 52 is advanced through the introducer sheath 64 to a dilatation area in the vasculature.

When the distal end 54 of the outer catheter 52 is at a location downstream of the dilatation area in the body vessel, the inner catheter 42 is inserted therethrough to the dilatation area. The device 10 is then loaded at the proximal end of the inner catheter 42 and is advanced through the inner lumen thereof for deployment through its distal end. In this embodiment, the proximal stem is used to mechanically advance or push the device 10 through the catheter.

Figure 4:
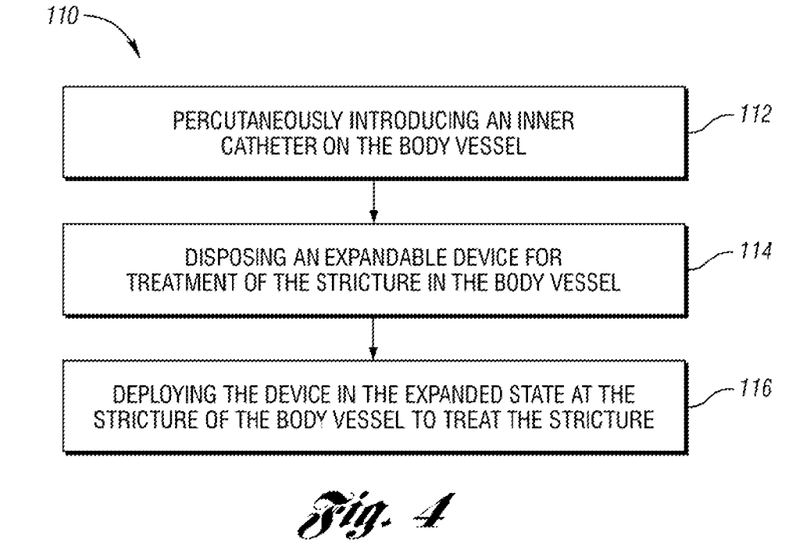
FIG. 4 is a flowchart of a method for treating a stricture in a body vessel in accordance with one example of the present invention.
Figures 5A, 5B:
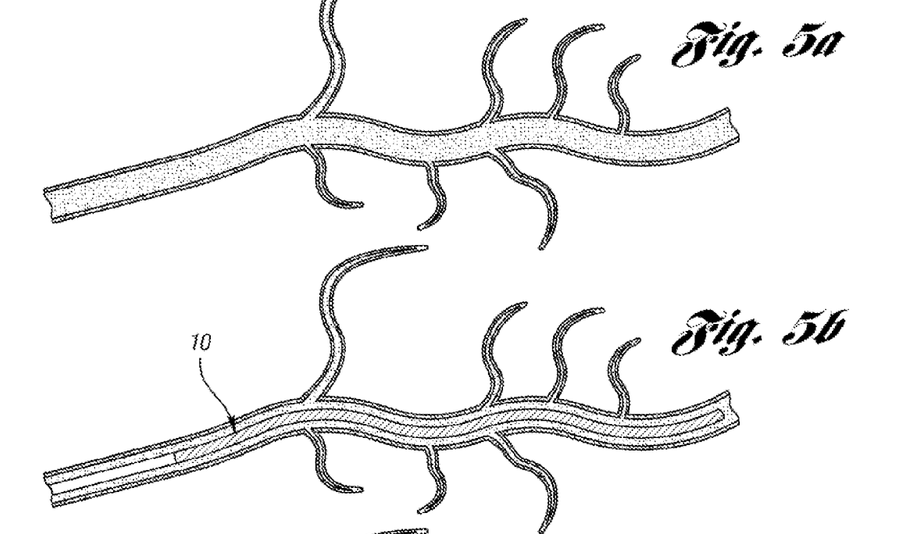
FIGS. 5a-5d are environmental views of treating a stricture with the expandable device.

FIG. 4 illustrates a flow chart depicting one method 110 for treating a stricture in a body vessel (see FIG. 5a), implementing the assembly mentioned above. The method comprises percutaneously introducing an inner catheter in the body vessel in box 112. Introduction of the inner catheter may be performed by any suitable means or mechanism. As mentioned above, an introducer sheath and a wire guide may be used to provide support and guidance to the inner catheter. For example, the wire guide may be percutaneously inserted through the introducer sheath to the stricture in the body vessel. The inner catheter may then be place over the wire guide for percutaneous guidance and introduction to the stricture.

The method 110 further comprises disposing the expandable device coaxially within the inner catheter in box 114. The device may be disposed coaxially within the inner catheter before or after percutaneous insertion of the inner catheter. Preferably, the expandable member is disposed along a longitudinal axis. For example, once the inner catheter is placed at the stricture of the body vessel, the wire guide may be removed therefrom, and the device may then be disposed within the inner catheter for guidance and introduction in the body vessel. In the collapsed state, the device may then be advanced distally past the inner catheter in the body vessel (see FIG. 5b).

As mentioned above, the expandable member is helically closed in the collapsed state when the tubular portion is rotated about the longitudinal axis in a first direction and the expandable member is helically opened in the expanded state when the tubular portion is rotated about the longitudinal axis in a second direction.

Figures 5C, 5E:
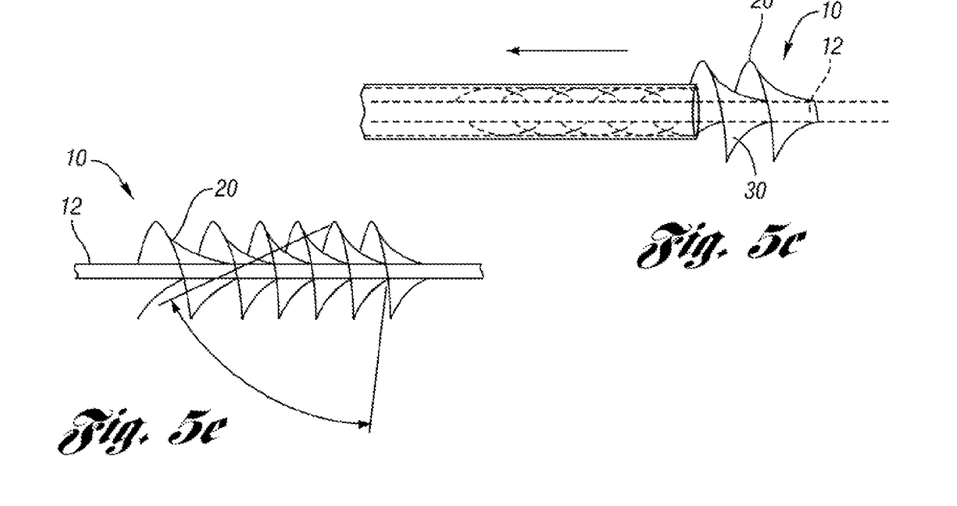
FIG. 5e is an enlarged view of the expandable device in FIG. 5d.
Figure 5D:
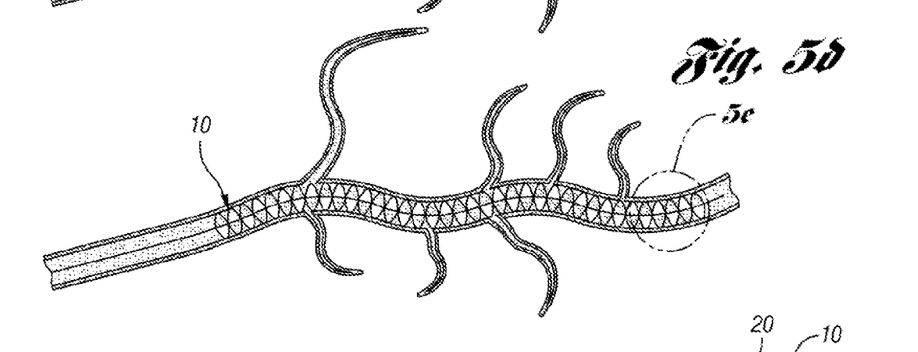

The method 110 further includes deploying the device in the expanded state in box 116 (see also FIG. 5c). This may be accomplished by pushing the device by any suitable means such as a pusher. In this example, the device is self-expanding and is configured to turn about a first direction relative to the tubular portion to helically open and treat the stricture in the body vessel. In the expanded state, the open end of each member portion is expanded to a proximally facing concave shape to engage the body vessel for stenting. In this embodiment, each member portion extends from the tubular portion at an angle between about 40 and 70 degree (see FIGS. 5d and 5e). As desired, additional inner catheters may be used for primary and post-dilatation treatment of the stricture.

The method 110 further comprises closing the device in the collapsed state in the body vessel by rotating the tubular portion in the first direction and retrieving the device in the collapsed state in the inner catheter.

While the present invention has been described in terms of preferred embodiments, it will be understood, of course, that the invention is not limited thereto since modifications may be made to those skilled in the art, particularly in light of the foregoing teachings.

The invention claimed is:

1. An expandable device for treatment of a stenotic lesion in a body vessel, the device comprising:
   a tubular portion including a proximal end and a distal end extending from the proximal end, the tubular portion having a lumen formed therethrough between the proximal and distal ends; and
   an expandable member formed helically about the tubular portion, the expandable member being configured to helically close defining a collapsed state for delivery of the device, the expandable member being configured to helically open defining an expanded state, in which the expandable member forms an outermost periphery of the expandable device, for treatment of the stenotic lesion in the body vessel, the expandable member having at least one member portion helically extending from the tubular portion at a predetermined angle at the outermost periphery, defining a proximally faced opening having a concave shape with the predetermined angle forming a greater opening angle than an opening angle adjacent the tubular member when the expandable member is in the expanded state, the predetermined angle being between about 40 and 70 degrees.

2. The device of claim 1 wherein the predetermined angle is between about 55 and 65 degrees.

3. The device of claim 1 wherein the at least one member portion is a plurality of member portions.

4. The device of claim 3 wherein each of the plurality of member portions is in coaxial alignment with each other about the tubular portion.

5. The device of claim 1 wherein the expandable member is disposed along a longitudinal axis, the expandable member being helically closed in the collapsed state when the tubular portion is rotated about the longitudinal axis in a first direction and the expandable member is helically opened in the expanded state when the tubular portion is rotated about the longitudinal axis in a second direction.

6. The device of claim 1 wherein the expandable member comprises at least one of the following materials:
   superelastic material, nitinol, polymeric material.

* * * * *